United States Patent
Schmidt et al.

(10) Patent No.: US 8,488,855 B2
(45) Date of Patent: Jul. 16, 2013

(54) TRANSPORTABLE PET INSERT (75) Inventors: Sebastian Schmidt, Weisendorf (DE); Jürgen Kampmeier, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1537 days.

(21) Appl. No.: 11/787,625

(22) Filed: Apr. 17, 2007

(65) Prior Publication Data
US 2008/0260104 A1 Oct. 23, 2008

(51) Int. Cl.
*G06K 9/00* (2006.01)
(52) U.S. Cl.
USPC .................................. 382/131; 705/3
(58) Field of Classification Search
USPC .............................. 705/3; 382/131
See application file for complete search history.

(56) References Cited

U.S. PATENT DOCUMENTS 7,001,330 B2 * 2/2006 Kobayashi ................ 600/118
2006/0251312 A1 * 11/2006 Krieg et al. ................ 382/131

OTHER PUBLICATIONS

US Federal Trade Commission Annual Report, 1990, Part II (Investigative Stage) Consent Orders Issued, Maintaining Competition Mission, p. 28.*

* cited by examiner

*Primary Examiner* — Michael Fuelling
(74) *Attorney, Agent, or Firm* — Lempia Summerfield Katz LLC (57) ABSTRACT

Methods and features of a transportable PET insert unit are disclosed. A transportable PET insert unit is provided. The transportable PET insert unit is operable to be coupled with a non-PET imaging system. The transportable PET insert unit is rented to a client.

19 Claims, 5 Drawing Sheets

TRANSPORTABLE PET INSERT

BACKGROUND

The present invention relates to medical imaging. In particular, a positron emission tomography insert unit is provided.

Medical imaging techniques and processes are used to create images of internal features of humans, animals, and other objects. The images are used for clinical purposes, such as examining and diagnosing disease or injury, as well as medical science, such as studying normal anatomy and function. Medical imaging includes, but is not limited to, magnetic resonance tomography ("MRT") or imaging ("MRI"), positron emission tomography ("PET"), and computed tomography ("CT"). Hybrid modalities, such as PET-CT and MRI-PET, are gaining increasing importance in medical imaging. The hybrid modalities combine two different imaging methods into one piece of equipment and can be used to perform separate scans for each individual method or integrated scans to create superimposed images.

However, the utilization of the individual components of hybrid modalities is highly different. For example, fewer PET scans are usually performed compared to CT or MRI scans. Also, PET scans occur at very limited times because the half-life of the radiopharmaceuticals used for PET scans, such as Fluorodeoxyglucose, ("FDG"), is very brief (e.g., a few hours). Because of this, expensive PET components may be unused most of the time at client sites.

One approach is to mount hybrid systems, such as PET-CT scanners, on a truck and drive them from client to client. However, in this case, the CT scanner, which is used frequently, is only available to a client at a certain time. Therefore, clients are then compelled to purchase a separate CT scanner or wait for the next time a hybrid system is available.

BRIEF SUMMARY

By way of introduction, the preferred embodiments described below include an imaging system, a transportable PET insert unit, and methods of renting the transportable PET insert unit. The transportable PET insert unit can be rented to a client and used in conjunction with a client owned imaging system.

In a first aspect, a computer-readable medium having stored therein instructions executable by a processor is provided. The instructions comprise determining a time period that a transportable PET insert unit is rented and generating a bill based on the time period. The transportable PET insert is insertable within a MRI system.

In a second aspect, a method of renting a transportable PET insert unit is provided. A transportable PET insert unit is provided. The transportable PET insert unit is operable to be coupled with a non-PET imaging system. The transportable PET insert unit is rented to a client.

In a third aspect, a method of renting a transportable PET insert unit is provided. A transportable PET insert unit is provided. Installation of the transportable PET insert unit in a MRI system of a first client is provided. The first client is charged for the transportable PET insert unit. Removal of the transportable PET insert unit from the MRI system of the first client is provided. Installation of the transportable PET insert unit in a MRI system of a second client is provided. The second client is charged for the transportable PET insert unit.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An imaging system is divided into a mobile part and a stationary part. The stationary part includes, but is not limited to, an MRI system, shielding devices, cables and cable leadthroughs, and cooling systems. The mobile part is a transportable PET insert unit. The computer systems required for the PET or the MRI-PET system and processing electronics can be designed as either stationary or transportable. For example, the PET computer system may be integrated into the MRI computer system. The transportable PET insert unit is used for a plurality of MRI-PET systems. The transportable PET insert unit is made available for Client A on some days of the week and is made available for Client B on the other days of the week. Also, the clients can be billed for actual use of the transportable PET insert unit or a time that the transportable PET insert unit is installed at the client site.

Figure 1:
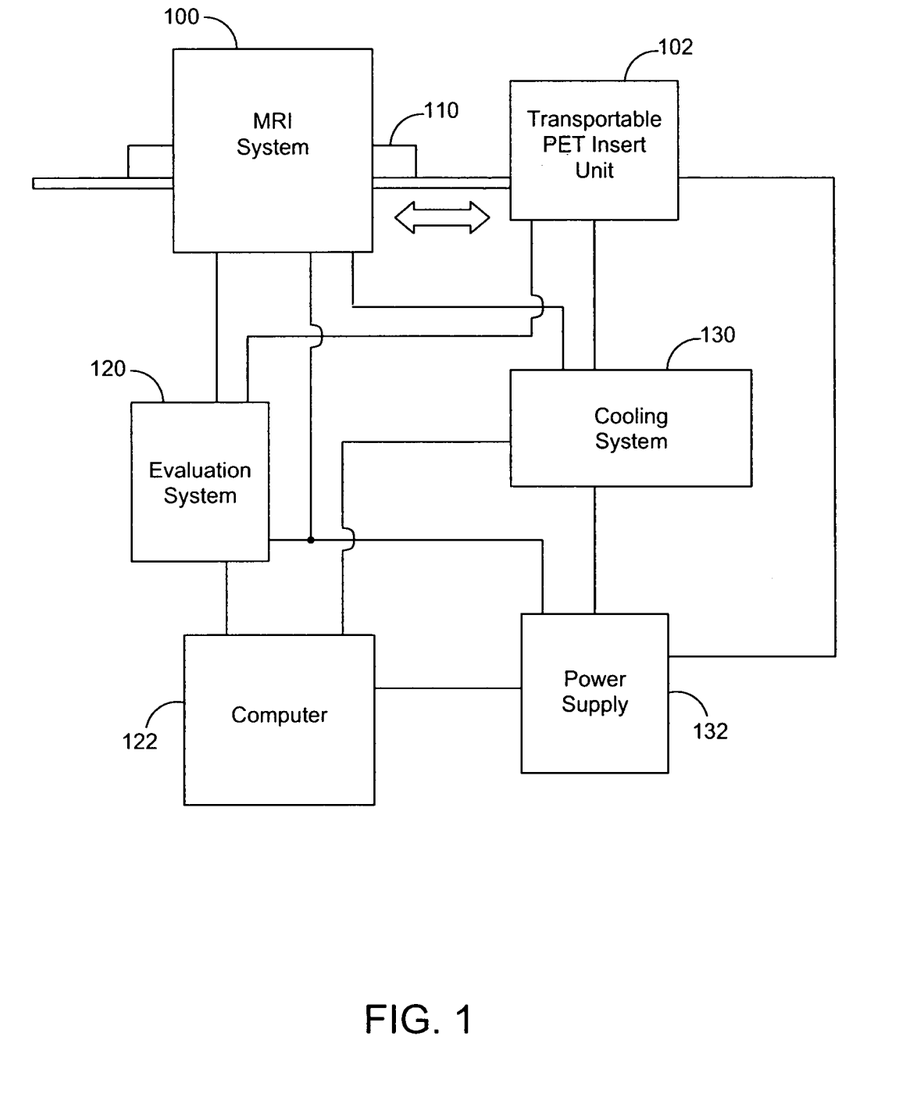
FIG. 1 is a diagram of one embodiment of an imaging system using a transportable PET insert unit.

FIG. 1 shows one embodiment of an imaging system using a transportable PET insert unit. The imaging system includes, but is not limited to, a MRI system 100, a transportable PET insert unit 102, an evaluation system 120, a computer 122, a power supply 132, and a cooling system 130. Additional, different, or fewer components maybe provided. The imaging system generates images of an object 110. The object 110 is a human, animal, or any other living or non-living thing that can be scanned for imaging purposes.

The MRI system 100 is a MRI or MRT scanner. The MRI system 100 includes, but is not limited to, coils for generating a fundamental magnetic field, a gradient coil system for generating independent, mutually perpendicular magnetic field gradients, and a high frequency antenna for generating excitation pulses and/or for receiving magnetic resonance signals from the object 110. The MRI system, for example, is used to create internal images of a human being based on the magnetic resonance signals. Any now know or later developed MRI system may be used.

The transportable PET insert unit 102 can be coupled to the MRI system 100. For example, the transportable PET insert unit 102 is of annular configuration and can be inserted or arranged concentrically in a cavity or bore of the MRI system 100. Alternatively, the transportable PET insert unit 102 may be connected to an outer or peripheral portion of the MRI system 100. The transportable PET insert unit 102 includes, but is not limited to, a gamma ray detector for detecting radiation emitted by the object 110 and a shielding cover. United States Patent Application US 2006/0251312 A1, which is hereby incorporated by reference, further describes the interconnection and integration between a MRT unit and a PET unit part.

The transportable PET insert unit 102 generates internal images of the object 110 based on positron emission decay. For example, a short-lived radioactive tracer isotope or radiopharmaceutical, which decays by emitting a positron, is injected into a human body. Then the transportable PET insert unit scans the object 110 to produce a three-dimensional image or map of anatomy or functional processes in the body. A commonly used radiopharmaceutical is Fluorodeoxyglucose, ("FDG").

When the transportable insert unit 102 is inserted or installed in the MRI system 100, a variety of images can be generated. For example, individual MRI images can be generated or individual PET images can be generated. The images may be acquired sequentially. Also, the MRI system 100 and the transportable insert unit 102 can be operated simultaneously to generate combined, superimposed or separate images.

The evaluation system 120, which is connected with the MRI system 100 and the transportable PET insert unit 102, aids in creating PET and MRI images. The evaluation system may be separated into two evaluation units or may be incorporated into the computer 122. The computer 122 is connected with the evaluation system 120 and is used to control the operation of the MRI system 100 and the transportable PET insert unit 102. The computer 122 also includes a display to view the generated images, a network connection for transfer or storage of images, and/or a memory for storage of the images.

The cooling system 130, coupled with the MRI system 100 and the transportable PET insert unit 102, provides cool air or fluid, such as water, via tubes or piping to the MRI system 100 and/or the transportable PET insert unit 102. Physical channels or ducts in the MRI system 100 and/or the transportable PET insert unit 102 allow cool air or fluid to pass through the respective structures to dissipate heat generated during operation. The cooling system may have its own computer system or may be controlled by the computer 122.

The power supply 132 is connected with the MRI system 100, the transportable PET insert unit 102, the evaluation system 120, the computer 122, and the cooling system 130 to provide power for operation. The power supply 132 may be split into a number of power sources for each respective component. Also, the electrical interconnections and cables as well as the mechanical tubes and pipes are designed as pluggable inserts that can be removed and inserted with convenience. Alternatively, cables and tubes that are designed to be stationary may be fixed connections that need not be removed.

The MRI system 100 and the transportable PET insert unit 102 are placed in a shielding room that acts as a Faraday cage as well as a shield for gamma radiation. The other components of the imaging system, such as the evaluation system 120, the computer 122, the cooling system 130, and the power supply 132 are placed outside the room minimizing the number of electronics exposed to the generated magnetic and associated fields. Any combination of components inside or outside the room may be arranged.

Even though the imaging system of FIG. 1 shows a hybrid MRI system 100 and transportable PET insert unit 102, any combination of medical imaging may be used. For example, a MRI-CT or CT-PET can be combined where any of the individual components are transportable.

Figure 2:
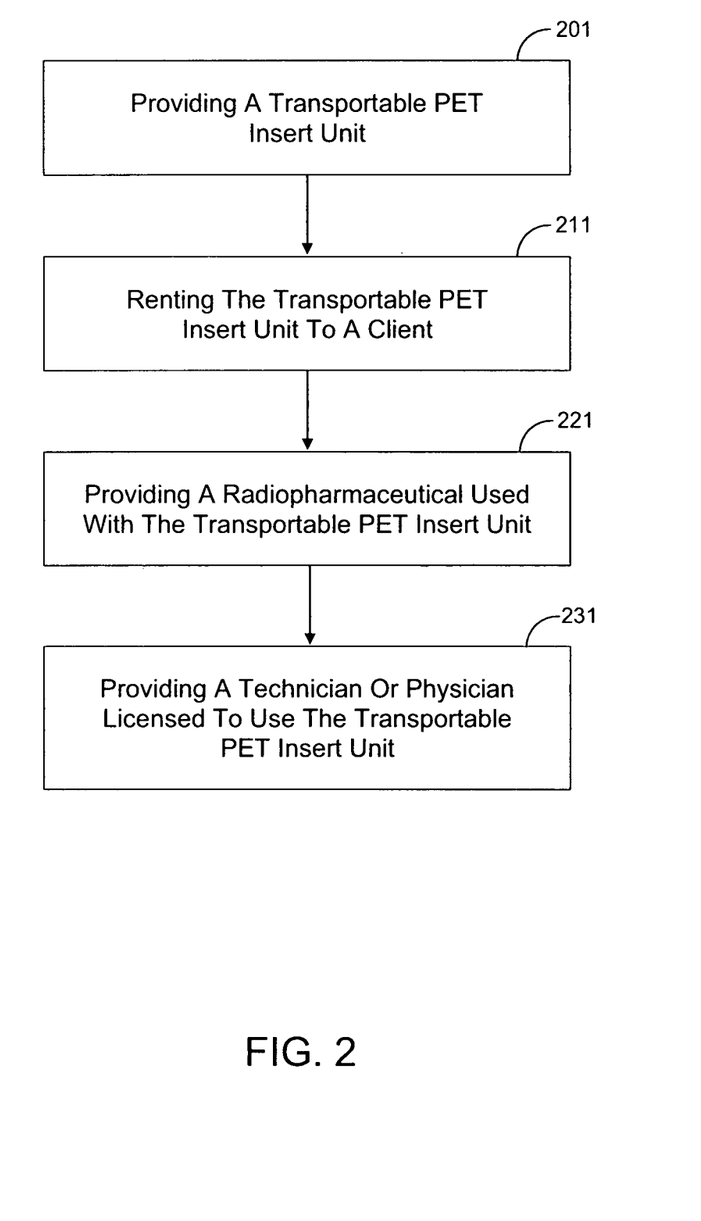
FIG. 2 is a flowchart of one embodiment of a method of renting a transportable PET insert unit.

FIG. 2 shows one embodiment of a method of renting a transportable PET insert unit 102. In act 201, a transportable PET insert unit, such as transportable PET insert unit 102, is provided. The transportable PET insert unit can be provided by the lessor, original manufacturer, or any other entity.

In act 211, the transportable PET insert unit is rented to a client. The owner of the transportable PET insert unit rents the unit to the client for any number of days. For example, the transportable PET insert unit is rented to the client for at least one day or at most one day. The same transportable PET insert unit may be rented to multiple clients. For example, a first client rents the unit for Monday and Tuesday and a second client rents the unit for Wednesday and Thursday of the same week. On days a client does not have the transportable PET insert unit, it can perform scans using its stationary MRI or CT scanner, and a required amount of FDG can be furnished at a time when the client will have possession of the transportable PET insert unit. The transportable PET insert unit is transported to a client site by land vehicle, such as a truck, boat, airplane, helicopter, or any other transport.

Part of renting the transportable PET insert unit to a client is installing the unit at the client site. The lessor provides employees to physically install the transportable PET insert unit into a non-PET imaging system, such as the MRI system 100. Alternatively, the lessor may provide for a third party installation service to install the transportable PET insert unit or the client may install the unit itself. The time it takes to install the transportable PET insert unit is short to allow for easy and effective transportation from client site to client site. For example, the installing time is about a few hours or at most about 2 hours. The PET insert is physically placed within the stationary imaging system and attached. Cables and/or cooling connections are made to integrate the PET insert.

The transportable PET insert unit is transported to the client site during a business day, a weekend day, or overnight before the business day begins. For example, a first client uses the transportable PET insert unit on a Monday morning. The transportable PET insert unit is in transit Monday evening headed to a second client site. The transportable PET insert unit arrives at the second client site before regular business hours and is installed to be ready for use for the first appointment on Tuesday.

Part of renting the transportable PET insert unit to a client also includes, but is not limited to, removing the unit from the client site. The lessor provides employees, which may be the installation employees or different employees, to physically remove the transportable PET insert unit from a non-PET imaging system. Alternatively, the lessor may provide for a third party removal service, which may be the third party installation service or a different service, to remove the transportable PET insert unit or the client may remove the unit itself. Removal takes place in the afternoon, after business hours, or any other time in a 24 hour day.

Any number of components associated with the transportable PET insert unit may be rented to a client as well. For example, a computer, such as computer 122, electronics, shielding devices, and/or cooling systems, such as cooling system 130, or any other imaging system component discussed above is rented to a client in conjunction with the transportable PET insert unit. Upgrades, boosters or additional components (e.g., a further cooling system 130 to handle the additional load) may be rented or sold for use with the transportable PET insert unit. However, components that are not costly, that are difficult to transport, or that the client acquired may be owned and kept at the client site.

The details of renting a transportable PET insert unit between the lessor and a client are covered in a rental agreement or contract. The rental contract includes, but is not limited to, terms concerning days when the client will use the transportable PET insert unit, timings of installation and removal, whether additional components will be rented, whether a technician or physician will be provided, whether a radiopharmaceutical will be provided, billing procedures, and/or cost. A rental contract of a transportable PET insert unit is executed between a lessor and a client when the lessor visits the client site. For example, a lessor visits a client site to sell a non-PET imaging system, such as the MRI system 100. Based on the purchase of the non-PET imaging system, a rental contract for the transportable PET insert unit is created. Alternatively, a client may rent a transportable PET insert unit absent a purchase of a non-PET imaging system. Communications between a lessor and a client in regards to renting a transportable PET insert unit and a rental contract may be accomplished via email, telephone, facsimile, and/or computer web page for renting a transportable PET insert unit.

There are a variety of ways for billing or charging a client for renting a transportable PET insert unit. For example, a client is billed for a time period that a transportable PET insert unit is rented. The time period is the time from installation, arrival, or beginning of transport of the transportable PET insert unit until removal, pick-up, or ending of transport. Alternatively, the time period for billing is the period of use of the transportable PET insert unit. For example, the transportable PET insert unit is installed into a non-PET imaging system at 8:00 am on any given day and is removed at 5:00 pm on the same day. However, the transportable PET insert is used only for 2 hours, 10:00 am to 12:00 pm. Depending on the rental contract, the client may be billed for the entire nine hours or may be billed for only two hours. The client is billed at a fixed cost rate. For example, a certain amount of dollars per hour is used to generate a bill based on the time period of use or the time period from installation to removal. A varying cost rate may be used where the cost rate changes based on what days of the week the transportable PET insert is rented, at what times it is rented, when installation and removal take place, number of uses, number of PET insert units rented, other contractual relationships, and/or the length of use.

Alternatively, a client is billed for types and quantity of actions performed by the transportable PET insert unit. Actions include, but are not limited to, scanning a patient and generating a PET image. For example, a client is billed for the number of images made, the number of patients scanned, the degree of measurement volume scanned, and/or running protocols. The client is charged a fixed cost per action. Alternatively, the client may be charged a varying cost per action. For example, a more complicated and resource intensive procedure may cost more than a less complicated procedure.

Additional costs and fees are incorporated in renting a transportable PET insert unit. For example, a client is charged a one time rental fee, overhead charges, separate installation and removal fees, special proprietary software fees, and any other additional fee. Also, the cost of radiopharmaceuticals as well as licensed technicians or physicians are incorporated into the cost per time or cost per action mentioned above. Alternatively, the cost of the radiopharmaceuticals and licensed technicians or physicians are additional fees. In one embodiment, a transportable PET insert unit is rented to a client for no cost upon the conclusion of a contract for purchasing a defined quantity of radiopharmaceuticals. In an alternate embodiment, a transportable PET insert unit is made available to a client for testing at no cost. Any number of combinations of fixed or varying costs of components, actions, radiopharmaceuticals, and technicians or physicians for renting a transportable PET insert unit discussed above may be used to bill or charge a client.

In act 221, a radiopharmaceutical, such as FDG, is provided with the transportable PET insert unit when a client rents the unit. A client knows what days the transportable PET insert unit will be available and can order an amount of the radiopharmaceutical that is appropriate depending on how many patients are planning on having PET scans. The radiopharmaceutical arrives with the transportable PET insert unit or may arrive at a different time via mail or delivery. Alternatively, the client orders the radiopharmaceutical separate from any rental agreement for the transportable PET insert unit.

In act 231, a technician or physician licensed to use the transportable PET insert unit is provided when the client rents the unit. The technician or physician is trained in radiology, nuclear medicine, and/or any other field of medicine. The technician or physician may be an employee of the lessor or may be from a third party source. The technician or physician arrives at the client site to operate or supervise PET scans by the transportable PET insert unit. Alternatively, the client can have its own technician or physician that is licensed to use the transportable PET insert unit.

Figure 3:
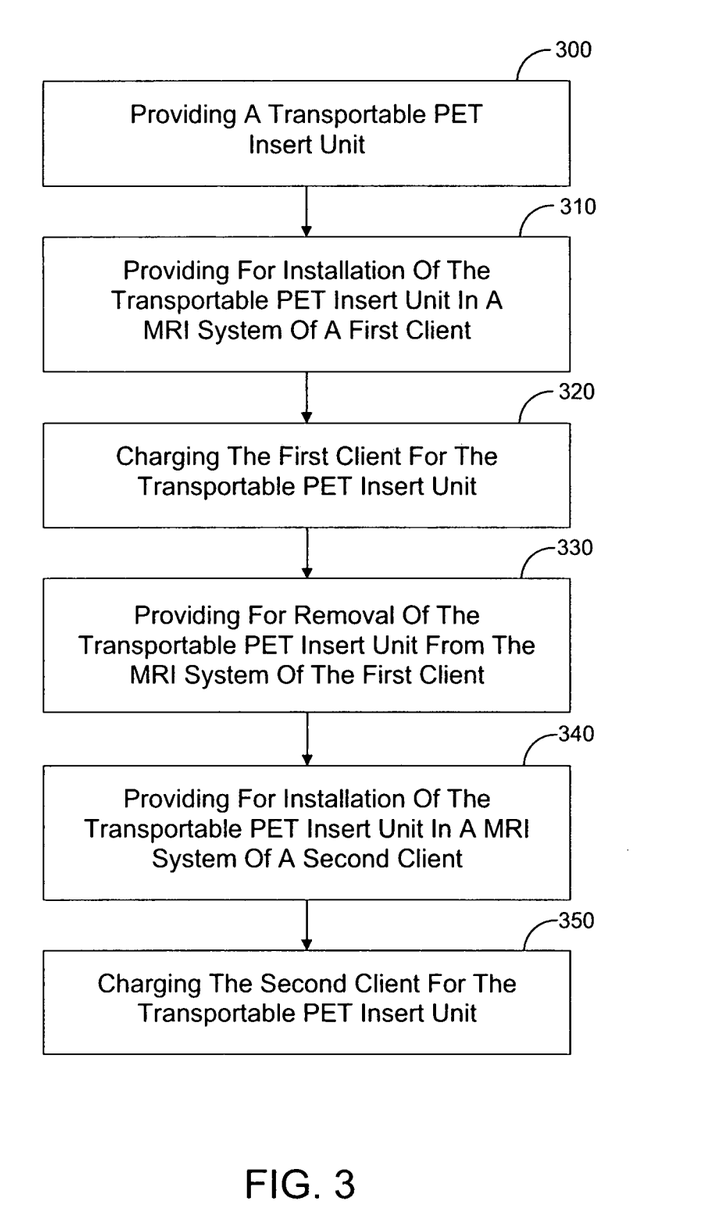
FIG. 3 is a flowchart of an example of another method of renting a transportable PET insert unit.

Any of the methods and acts of renting a transportable PET insert unit to a client mentioned above can be mixed and matched. For example, FIG. 3 is an example of a method of renting a transportable PET insert unit, such as the transportable PET insert unit 102. In act 300, a lessor provides a transportable PET insert unit. In act 310, the lessor provides for installation of the transportable PET insert unit in a MRI system, such as the MRI system 100, of a first client. Installation is conducted by the lessor's employees or a third party. In act 320, the lessor charges the first client for the transportable PET insert unit. The client may be charged for a time period or for specific actions at varying or fixed costs. Any number of the billing techniques discussed above are applicable. In act 330, the lessor provides for removal of the transportable PET insert unit from the MRI system of the first client. The time between installing and removing the transportable PET insert unit for the first client is within about 24 hours or other longer or shorter time period. In act 340, the lessor provides for installation of the transportable PET insert unit in a MRI system of a second client. The method of installation for the second client may be the same or different than for the first client. In act 350, the lessor charges the second client for the transportable PET insert unit. The method of charging the second client may be the same or different than for the first client. A client pays any bill associated with renting the transportable PET insert unit using current payment methods or any future payment methods. For example, a client pays a generated bill by cash, check, credit card, direct deposit, and/or through wireless or internet database options.

Figure 4:
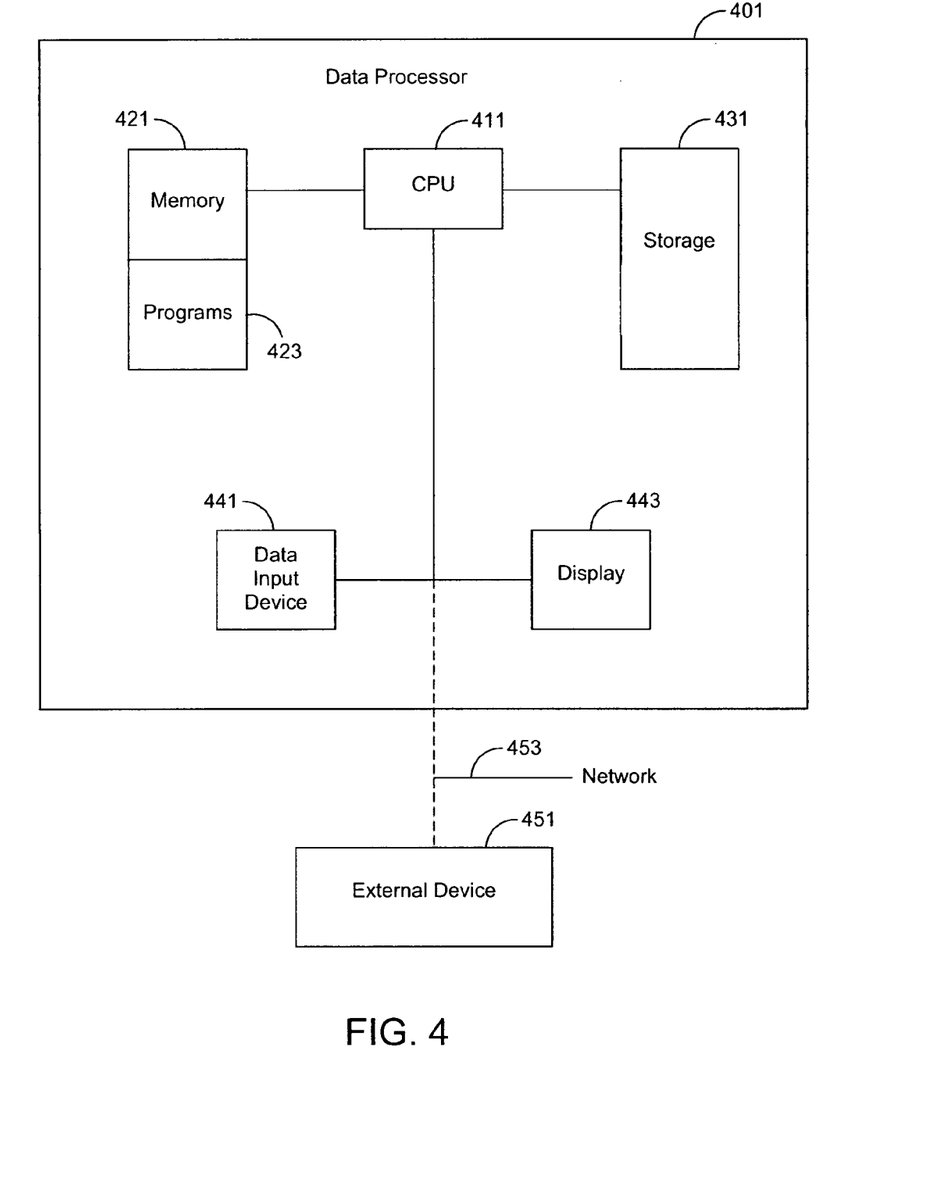
FIG. 4 is a diagram of one embodiment of a data processor that can be used in conjunction with the transportable PET insert unit of FIG. 1.

FIG. 4 shows one embodiment of a data processor 401 used in conjunction with the transportable PET insert unit of FIG. 1. The data processor is the computer 122, a part of the computer 122, or a separate system, such as a personal computer, work station, picture archiving and communication system ("PACS") station, the MRI system 100, part of the MRI system 100, the transportable PET insert unit 102, part of the transportable PET insert unit 102, or other medical imaging system. The data processor 401 includes, but is not limited to, a central processing unit (CPU) 411, a memory 421, a storage device 431, a data input device 441, and a display 443. The data processor 401 is in communication with an external device 451 via a network 453. The external device 451 is the MRI system 100, the transportable PET insert unit 102, the combination of both, and/or another computer system, such as computer 122. The network 453 is a cable, wire connection, wireless connection, an intranet, the Internet, and/or an intranet connected to the Internet.

The data processor 401 is coupled with a user interface for presenting information and receiving instructions and/or user requests via the display 443, the external device 451, or other display. Herein, the phrase "coupled with" is defined to mean directly connected to or indirectly connected through one or more intermediate components. Such intermediate components include both hardware and software based components.

A program 423 resides on the memory 421 and includes one or more sequences of executable code or coded instructions that are executed by the CPU 411. The program 423 is loaded into the memory 421 from the storage device 431. The CPU 411 executes one or more sequences of instructions of the program 423 to process data. Data is input to the data processor 401 with the data input device 441 and/or received from the external device 451 via the network 453. The program 423 interfaces the data input device 441 and/or the external device 451 for the input of data. Data processed by the data processor 401 is provided as an output to the display 443, the external device 451, the network 453, and/or stored in a database, such as a vendor or lessor accessible database. The program 423 and other data may be stored on or read from machine-readable medium, including secondary storage devices such as hard disks, flash drives, RAM, cache, floppy disks, CD-ROMS, and DVDs; electromagnetic signals; or other forms of machine readable medium, either currently known or later developed.

The data processor 401 is used to control a transportable PET insert unit, such as transportable insert unit 102, and may control the other components of the imaging system of FIG. 1. The data processor 401 or a separate data processor is used for the billing techniques discussed above. For example, the lessor has a computer at its office or any location remote to the transportable PET insert unit to keep track of or monitor the uses and time periods associated with the transportable PET insert unit discussed above. The monitoring may occur substantially in real time.

Figure 5:
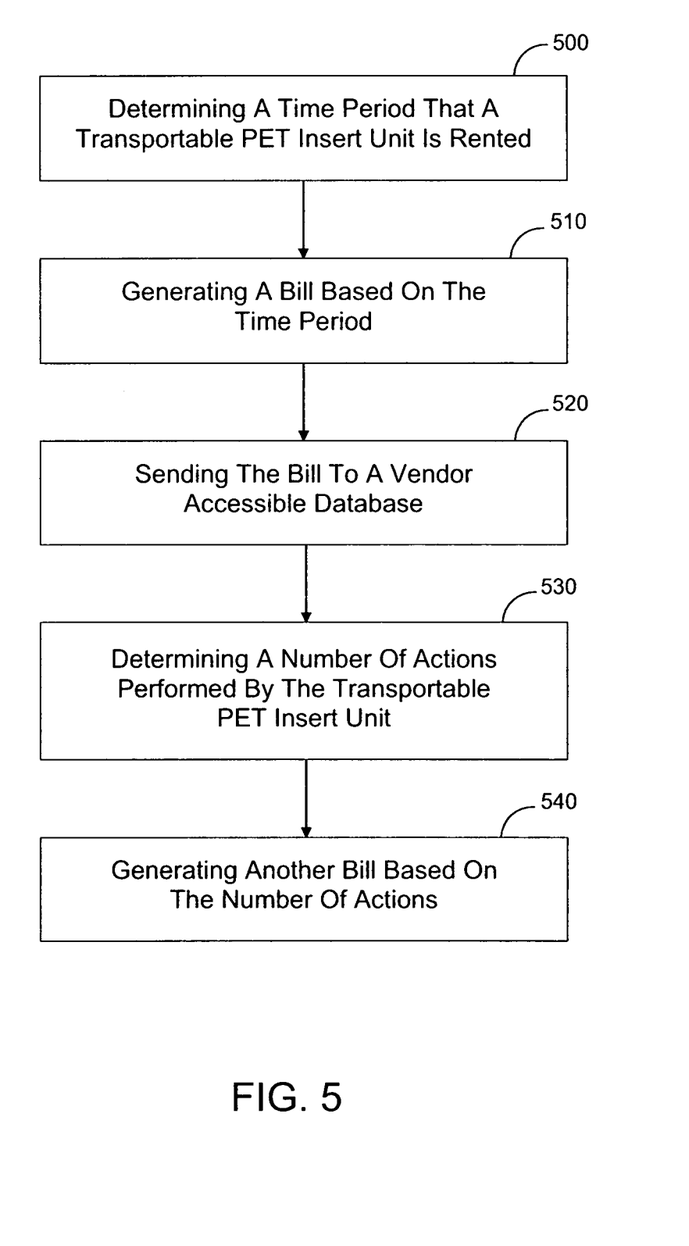
FIG. 5 is a flowchart of one embodiment of instructions that can be executable by the data processor of FIG. 4.

FIG. 5 shows a flowchart of one embodiment of instructions that can be executable by the data processor 401 of FIG. 4. In act 500, a time period that a transportable PET insert unit is rented is determined. The data processor monitors, determines, and stores the time of use or the time from installation to removal as mention above. One or more sensors are provided to detect installation, or activation or use of the data processor 401 may indicate completion of an installation. Since the data processor 401 controls scanning, the data processor 401 may store time of usage or type of usage. Alternatively, or additionally, a user may input parameters or variables (e.g., time of installation).

In act 510, a bill is generated based on the time period. For example, a fixed cost rate or a varying cost rate is multiplied with the respective time periods. Other methods of calculations may be performed. The data used for billing is gathered or indicated as missing. Once sufficient information is obtained by data transfer or user entry, the bill is generated. The bill may be reviewed and edited.

In act 520, the bill is sent to a vendor or lessor accessible database. For example, after a bill is generated, the data processor 401 transmits the bill information to a webpage or internet database via network 453 where the lessor can check the cost the client has incurred.

Additionally, the data processor 401 monitors and stores the number and/or type of actions the transportable PET insert unit performs, as in act 530. In act 540, another bill is generated based on the number and/or type of actions. For example, a fixed or varying cost that applies to a respective action is used to create the bill.

Even though the methods of renting discussed above concern a transportable PET insert unit, any component of a hybrid imaging system may be transportable and available to rent to a client. The features, methods, and techniques discussed above apply to transportable MRI insert units, transportable CT insert units, and other imaging components.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. In a non-transitory computer-readable medium having stored therein instructions executable by a processor, the instructions comprising:
   determining, by the processor, a time period that a transportable positron emission tomography (PET) insert unit is rented by a client at a client site, the transportable PET insert unit being insertable within a magnetic resonance imaging (MRI) system and being used with the MRI system to image an object at the client site;
   generating a bill based on the time period;
   determining, by the processor, another time period that the transportable PET insert unit is rented by another client at another client site, the transportable PET insert unit being insertable within another MRI system and being used with the other MRI system to image another object at the other client site; and
   generating another bill based on the other time period.

2. The instructions of claim 1, further comprising:
   sending the bill to a vendor accessible database.

3. The instructions of claim 1, wherein determining the time period comprises determining the time period from a time the transportable PET insert unit is installed in the MRI system to a time the transportable PET insert unit is removed.

4. The instructions of claim 1, wherein determining the time period comprises determining a period of use of the transportable PET insert unit.

5. The instructions of claim 1, further comprising:
   determining a number of actions performed by the transportable PET insert unit; and
   generating a bill based on the number of actions.

6. The instructions of claim 5, wherein one of the actions comprises generating a PET image or scanning a patient.

7. The instructions of claim 1, wherein generating the bill comprises calculating the bill using a fixed cost rate.

8. A method of renting a transportable PET insert unit, comprising:
   providing a transportable PET insert unit, wherein the transportable PET insert unit is operable to be coupled with a non-PET imaging system and operable to be coupled with another non-PET imaging system;
   renting the transportable PET insert unit to a client, wherein renting the transportable PET insert unit to the client comprises installing the transportable PET insert unit in the non-PET imaging system;
   imaging an object using the transportable PET insert unit and the non-PET imaging system;

removing the transportable PET insert unit from the non-PET imaging system;

renting the transportable PET insert unit to another client, wherein renting the transportable PET insert unit to the other client comprises installing the transportable PET insert unit in the other non-PET imaging system; and imaging another object using the transportable PET insert unit and the other non-PET imaging system.

9. The method of claim 8, wherein renting the transportable PET insert unit to the client comprises renting the transportable PET insert unit to the client for a day.

10. The method of claim 8, wherein the non-PET imaging system comprises a MRI or CT scanner.

11. The method of claim 8, wherein the installing is performed by a lessor.

12. The method of claim 8, further comprising:
providing a radiopharmaceutical used with the transportable PET insert unit.

13. The method of claim 12, wherein the radiopharmaceutical comprises Fluorodeoxyglucose.

14. The method of claim 8, further comprising:
providing a technician or physician licensed to use the transportable PET insert unit.

15. The method of claim 8, wherein a rental contract of the transportable PET insert unit is based on a purchase of the non-PET imaging system by the client.

16. The method of claim 8, wherein renting the transportable PET insert unit to the client comprises billing the client using a fixed cost rate.

17. A method of renting a transportable PET insert unit, comprising:
providing a transportable PET insert unit;
providing for installation of the transportable PET insert unit in a MRI system of a first client;
imaging an object using the transportable PET insert unit and the MRI system of the first client;
charging the first client for the transportable PET insert unit;
providing for removal of the transportable PET insert unit from the MRI system of the first client;
providing for installation of the transportable PET insert unit in a MRI system of a second client;
imaging another object using the transportable PET insert unit and the MRI system of the second client; and
charging the second client for the transportable PET insert unit.

18. The method of claim 17, wherein charging the first client comprises charging a fixed cost rate for a time period from installation to removal.

19. The method of claim 17, wherein a time of installing and removing the transportable PET insert unit for the first client is within about 24 hours.

* * * * *